United States Patent [19]

Massey

[11] Patent Number: 4,704,129

[45] Date of Patent: Nov. 3, 1987

[54] RESHAPABLE PROSTHESIS

[76] Inventor: Peyton L. Massey, 860 Gretna Green, Los Angeles, Calif. 90049

[21] Appl. No.: 629,484

[22] Filed: Jul. 10, 1984

[51] Int. Cl.⁴ .................. B29C 17/04; A61F 3/00; B28B 3/06

[52] U.S. Cl. .................................. 623/25; 623/32; 623/57; 128/89 R; 128/90; 264/222

[58] Field of Search ............... 128/89 R, 90; 264/222; 623/28, 32, 57

[56] References Cited

U.S. PATENT DOCUMENTS

| 3,377,416 | 4/1968 | Kandel | 264/222 |
| 3,662,057 | 5/1972 | Webster | 264/222 |
| 3,789,518 | 2/1974 | Chase | 264/222 |
| 4,019,505 | 4/1977 | Wartman | 264/222 |
| 4,397,701 | 8/1983 | Johnson | 264/222 |
| 4,473,421 | 9/1984 | Gustafsson | 3/4 |

OTHER PUBLICATIONS

Atlas of Limb Prosthetics, American Academy of Orthopaedic Surgeons, C. V. Mosby Co., 1981, pp. 59–62.

Primary Examiner—John Kight
Assistant Examiner—M. L. Moore
Attorney, Agent, or Firm—William H. Maxwell

[57] ABSTRACT

A prosthesis adapted to be formed and reformed to a model made of a person's body part, and comprised of a blank member of cured vinyl plastic or the like prepared for formation and reformation and to be softened to a plastic condition at raised temperature substantially below its previous curing temperature and brought into conformity with the model countours and permitted to return to room temperature for hardening, and thereafter stripped from the model for use.

8 Claims, 12 Drawing Figures

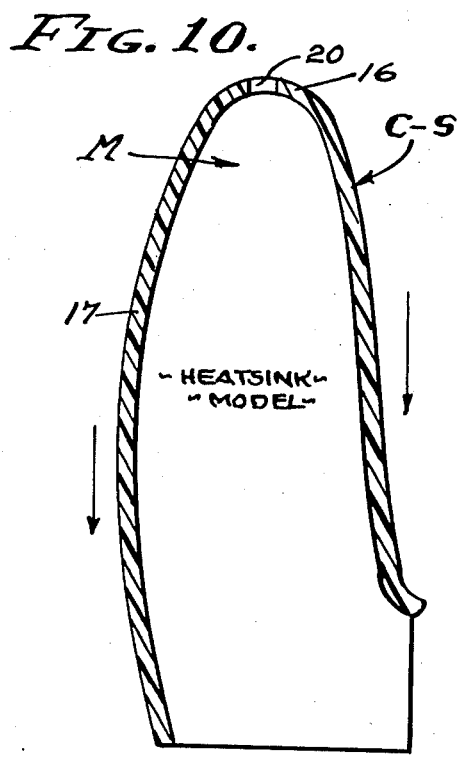
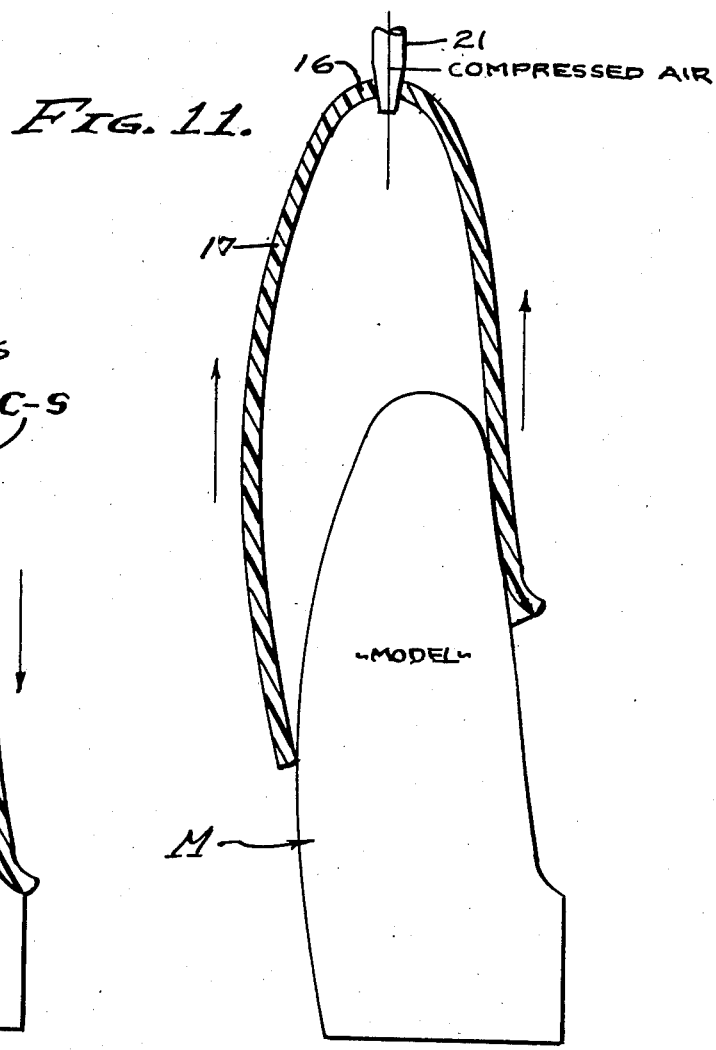
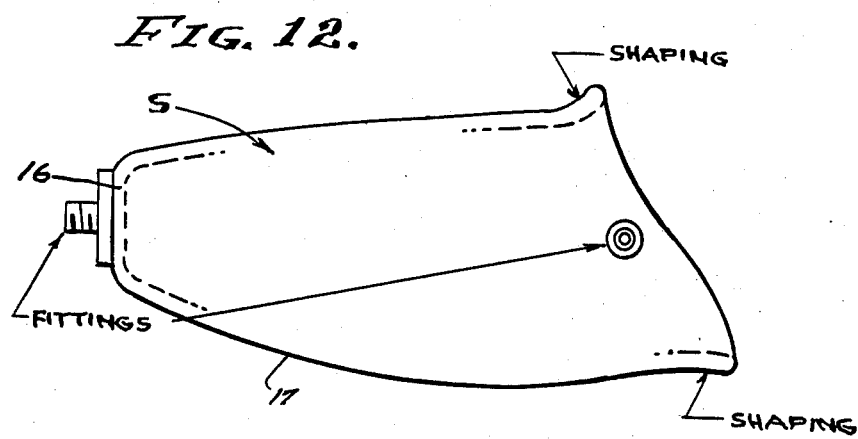

RESHAPABLE PROSTHESIS

CROSS REFERENCE

This application is a divisional of application Ser. No. 519,124, filed Aug. 1, 1983.

BACKGROUND

Prostheses are applied to the human body in order to replace amputated and/or deformed portions of the anatomy, and most often but not limited to the limbs. Essentially, it is missing portions that are to be simulated and fitted to the remaining parts or existing parts of the body. Consequently, there are contours of peculiar and abnormal configurations that must be matched and fitted to, and these can change in time. That is, there may be local swelling or shrinking of muscle and fatty tissue, and the underlying bone structure can change. Therefore, it is a general object of this invention to provide a prosthesis that is acurately fitted to the contours of the body, natural or abnormal, and which can be subsequently adjusted in its fit as circumstances require.

It is the limbs of the body that are most often injured and which are very necessary as members used in manipulation and ambulation. Therefore, this invention will be described as it relates to the arms and legs of amputees or the like, where a "stump" of the body limb is fitted for the application or the attachment of a prosthetic limb. Accordingly, it is an object of this invention to accurately fit a "socket" to the stump of a limb, not to exclude the fitting of any suitable prosthetic piece or form to the exterior of the body. In practice, an arm may be severed at or between the shoulder, elbow or wrist processes, and a leg may be severed at or between the hip, knee or ankle processes. The point of severence or amputation can be deliberate or by accident and in any case results in a "stump" of distinctive configuration that must be fitted to in each instance. Healing of the flesh over the terminated bone structure varies with each removal of the anatomy, and the prosthesis must be made special and/or customized to the individual stump or area to which it is to be attached. It is an an artcle of manufacture that inherenly conforms to body contours and configurations for the comfortable application and attachment of prostheses.

An object of this invention is to reduce expenditure in the process of producing prostheses conforming to body contours. Heretofore, inflexible firm prostheses have been made of materials that become permanent in shape and cannot be modified, except by removing or adding material thereto. For example, a limb socket made of resin impregnated fiberglass can be filed away or built up with added layers, but only with the expertise of an experienced craftsman; and even then the results are doubtfully beneficial. Furthermore, such individually prepared laminiform structures are expensive and their preparation is time consuming, requiring repeated sittings of the patient with the technician and at time intervals in order to allow for completion time in the finish work required. With the present invention a heated plastic member is prepared and fitted over a model made of a person's body part to be fitted. As shown herein the plastic member is a heated cone to be fitted over the model of a person's stump. The temperature applied is greater than that which can be tolerated by the skin of a person, and consequently a model of the body part or stump is employed in the process. The heated plastic conforms to the precise contours of the model and retains the model form when cooled to normal room temperature, at which time it is immediately fitted to the person and the required prosthesis features attached as may be required.

It is an object of this invention to provide a prosthesis that can be reshaped or reformed from time to time as required according to changes in the body part to which it fitted. To this end a partially cured plastic material is employed in forming the prosthesis, which is reformable at raised temperature below the curing temperature of said material, and which is structurally stable at lower normal ambient temperatures. The reforming temperature is greater than that which can be tolerated by the patient, and accordingly the model is retained for subsequent forming and reforming as the case may be. In the case of reforming, the model is reshaped, and being of plaster or the like, can be easily reshaped in a short length of time, while the patient is waiting. And, the prosthesis being of cured reshapable plastic material, it too can be quickly heated and easily reshaped over or to the modified model in a short length of time.

SUMMARY OF INVENTION

This invention relates to prostheses applied to the human anatomy, replacing amputated body parts or filling in voids caused by malformations. The purpose of this invention is to simplify the process of making the prostheses and to render them readily and immediately available to the patient to be worn. The prostheses as they will be described are essentially a monolithic monocoque structure, as distinguished from a structure of laminiform and constructed of multiple layers and/or parts. A feature of this invention is the cured condition of a plastic "blank" from which the prostheses are formed to the configuration of the models made from the patient's body part to which it is to be fitted. The forming and reforming of the prosthesis is at an elevated temperature below that of the curing temperature when preparing the plastic blank, and substantially above the ambient working temperature of the finished article. Accordingly, a process is involved in the preparation of said blanks, and in the steps of forming them into the aforesaid model from which they can be withdrawn over negative as well as positive draft angles. The prostheses produced herein are characteristically flexible and reshapable over the model therefor which can be modified as may be required. Also, the entry and/or perimeter openings for articulation can be shaped and sculpted to suit the patient's comfort, also by the application of heat below the curing temperature and positioned while cooling to set in the desired configuration.

The foregoing and various other objects and features of this invention will be apparent and fully understood from the following detailed description of the typical preferred form and application thereof, throughout which description reference is made to the accompanying drawings.

FIG. 2 showing the "slush cast" step of curing, FIG. 3 showing the stop bath, FIG. 4 showing the final curing, FIG. 5 showing the cooling to ambient temperature, and FIG. 6 showing the finally prepared cone.

Figure 1:
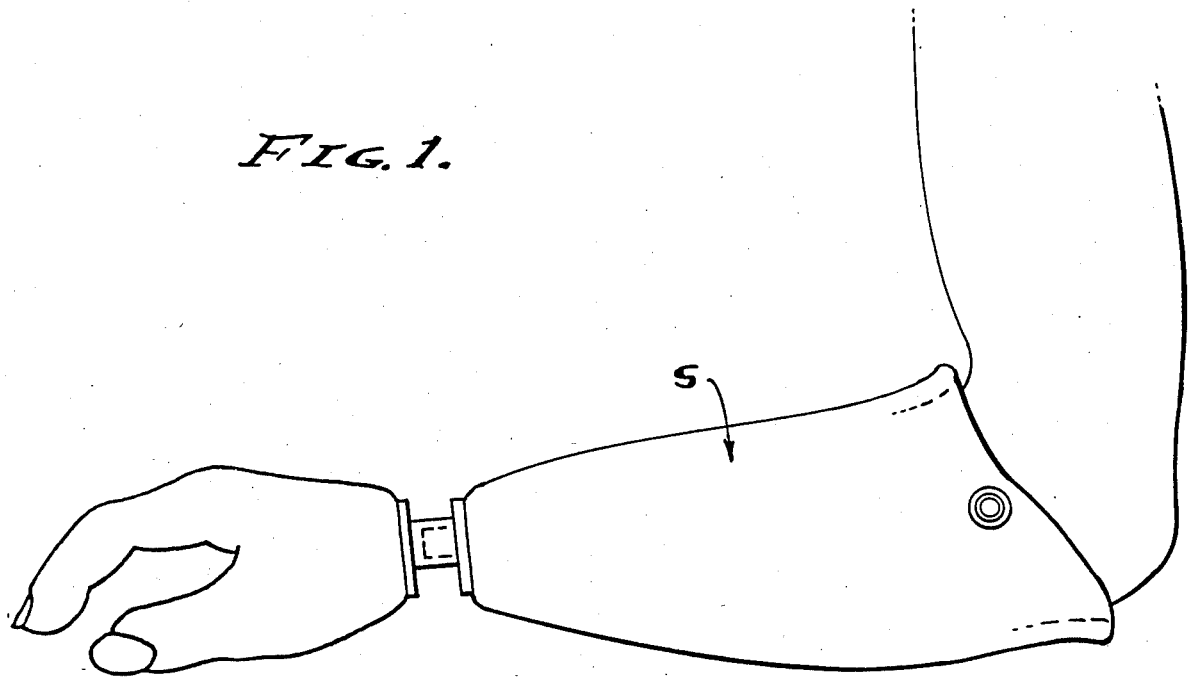
FIG. 1 is a side view of a hand and forearm prosthesis applied to an amputee.
Figure 2:
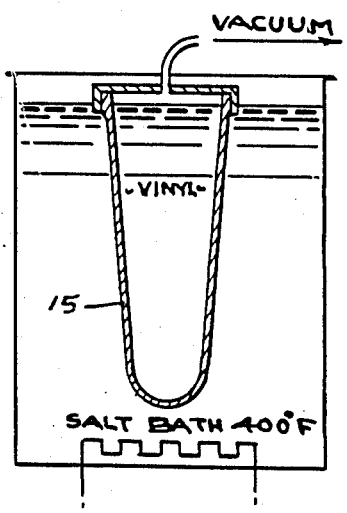
FIGS. 2 through 6 show the steps of preparing production blank members in the form of cones of cured plastic material for subsequent reformation.
Figure 3:
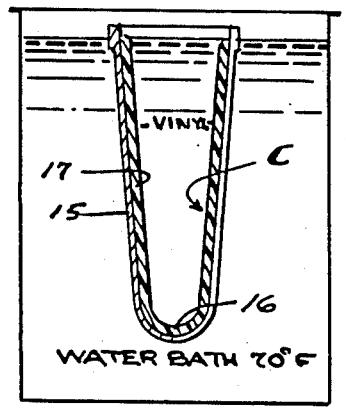
Figure 4:
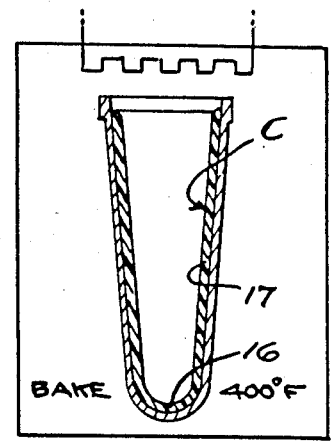
Figure 5:
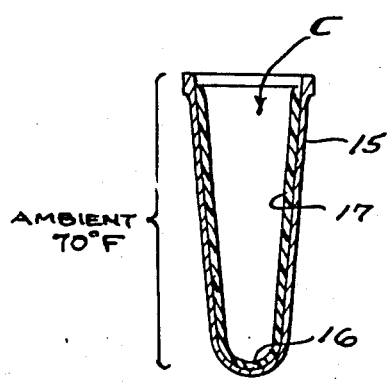
Figure 6:
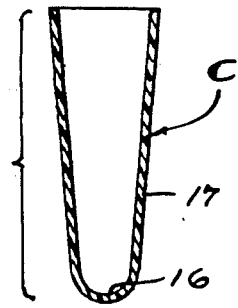
Figure 7:
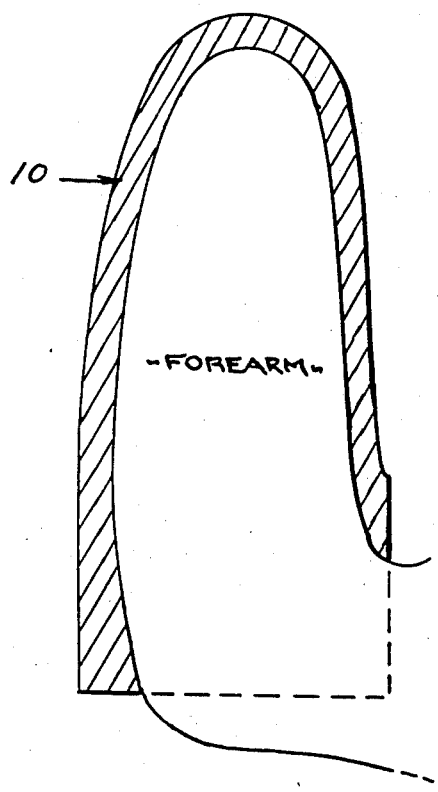
FIGS. 7 and 8 show the steps of preparing the model of an amputee's stub or the like., FIG. 7 showing the impression or cast of a forearm from which the hand has been amputated, and FIG. 8 showing a model made from the cast of FIG. 7, a model subject to sculpted reformation as circumstances require.
Figure 8:
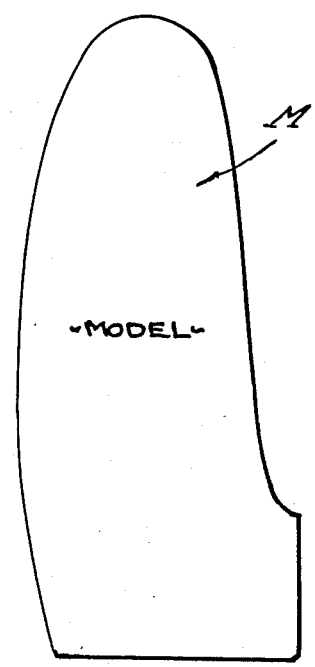
Figure 9:
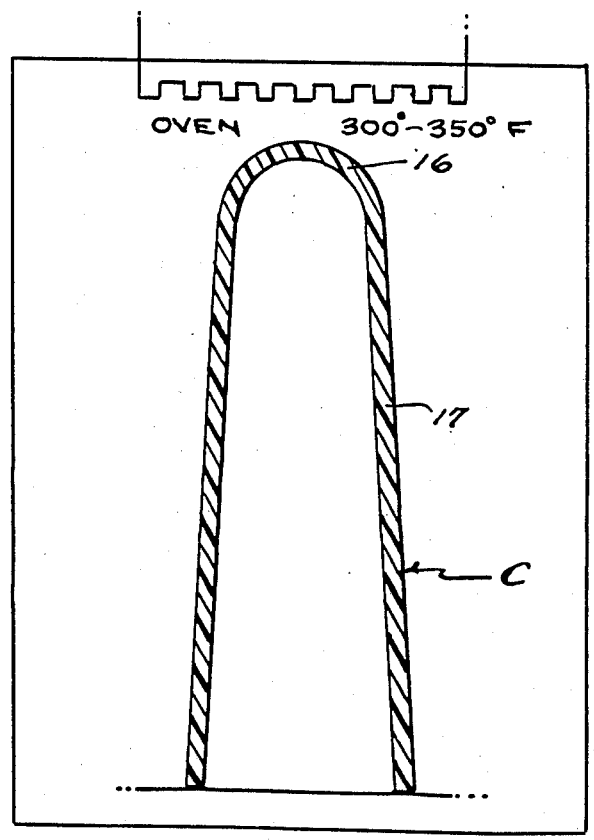

FIGS. 9 through 12 show the steps of preparing the prosthesis, a socket in this instance, FIG. 9 showing the step of plasticizing the prepared cone, FIG. 10 showing the constriction of the prepared cone onto the model of FIG. 8, FIG. 11 showing the stripping of the reformed cone from the model, and FIG. 12 showing the finished prosthesis socket shaped as circumstances require and with fittings attached as may be required.

PREFERRED EMBODIMENT

The reshapable prostheses will now be disclosed as they are formed upon models of body parts from blanks or cones that are prepared of cured plastic material and adapted to be reformed. The cured blanks or cones are produced as articles of manufacture in various configurations and sizes, to be subsequently formed and reformed over or within molds or models of the body part which they are to simulate as a prosthesis. It is to be understood that a model can be made of any amputation or void of the human anatomy and the blank member conformed thereto in the presence of heat and applied pressure. Accordingly, a most practical application of the present invention is in the conformity of sleeve shaped blanks onto male model configurations made from plaster casts of the patient's body parts to which the prostheses are to be fitted. These sleeve shaped blank members are hereinafter referred and shown in the drawings as a "cone", and the article of manufacture to be produced and distributed to prostheses makers and/or clinics where amputees are fitted therewith.

The primary object herein is the production of said blank members as articles and preferably in the form of cones C adapted to be subsequently shaped over a model of a person's stumped limb. The cone C as an article is prepared in various general sizes within a range adapted to conform with the arm and legs sizes of normal persons, children through adult as may be required. The number of cone sizes is minimized by the fact that the cured plastic, as it will be described, is readily stretched over a model M and easily cut and reformed to the size and configuration of the model. In practice, at least three or more sizes of cones C are contemplated, for example small, medium and large, or numbered sizes.

The first step in the process of making the model M is to take an impression of the amputee's body member or stump to which the prosthesis is to be applied. The second step is to duplicate the stump in the form of a model M that is molded in a cast 10 made by said first impression. The third step is to sculpt any relief or contour modifications into the model at the discretion of the technician who must adapt the prosthesis to the needs of the amputee. In practice, prior art methods are used in making the model M, for example employing the use of plaster of paris in making the impression 10 and model M cast therefrom, all of which is easily and quickly worked, and subsequently reshaped with facility.

The cone C is prepared as an article for subsequent use by the aforesaid technician in making a prosthesis therefrom. Characteristically, the cone C is a cured plastic single body monocoque sleeve adapted to be reworked under heat and pressure. The cone C is "slush cast" in a heat transfer mold 15, for example a Nickel vessel having an interior formed to the exterior configuration desired for the cone C. The raw plastic resin, plasticizer, stabilizer and pigment are mixed, for example, as follows, and poured into mold 15 at room temperature and filling said mold. A suitable Vinyl Resin 69.5% by volume is "Geon 121" as manufactured by Goodrich of Akron Ohio. A suitable Plasticizer 20.4% by volume is Dioctyl Phthate (DOP). And a suitable Stabilizer 9.4% by volume is "Mark 755" as manufactured by Argus Chemical. Any suitable inert pigment 0.7% by volume is used.

The mold 15 filled with the plastic mixture above described is vacuumized, and then heated to a curing temperature, in this instance 400° F. for a time period that will determine the "pick-up" or wall thickness of the cone C. In practice, heat is rapidly transferred into the mold 15 of Nickel by immersing it in molten salt at the aforesaid temperature. In carrying out this invention, the mold wall is 0.030 to 0.040 inch in thickness, in which case a 45 second immersion produces a ⅛ inch wall thickness, while a one (1) minute immersion produces a ¼ inch wall thickness. These are approximations. This pick-up step of the process is a partial curing step stopped by de-vacuumizing and immersing the filled mold into cold 70° F. water, which withdraws the heat sufficiently within three to five seconds, and after which the mold is drained of the uncured liquid plastic mixture. The uncured liquid plastic mixture is then reusable, as it was not affected by the previous application of heat.

The mold 15 containing the partially cured wall thickness of plastic material is then baked in an oven at said 400° F. curing temperature for approximately twenty-eight minutes. In practice, an air convection oven is used in this finishing step of curing the cone C. The mold 15 containing the completely cured plastic material is then removed from the oven and permitted to return to room temperature of, for example, 70° F. after which the finished cone C of structurally stable plastic is stripped from and removed from the mold 15. The finished cone C is characteristically a cured rigid plastic monoshell of tapered configuration terminating in an end wall 16 at its smaller end and open at its larger end. The wall 17 is of a specified thickness that is obtained as above described.

In accordance with this invention, a reshapable prosthesis S is subsequently made from the above described cone C by forming or reforming and resetting it to the configuration of the first described model M. In practice, a cone C commensurate in size with the model M is chosen, and preferably a cone slightly smaller in diameter, or circumference, than the model M. Accordingly, the secondary steps in the process of this prosthesis manufacture is the conforming of said blank member or cone C to the sculpted configuration of the model M made of the impression taken from the body part to be reproduced. The first step in the process of making the prosthesis socket S is to heat the selected cone C to a softening temperature substantially below the aforesaid curing temperature and in this instance to approximately 300° F. to 350° F., thereby establishing a softened plastic condition within the body of cured plastic material forming the walls 17 and end 16. In practice, an air convection oven is used in this preliminary heating step of preparing the cone C for its formation or reformation over the model M. Approximately five to ten minutes absorbtion time in a 300° F. or 350° F. oven is required for the plastic cone C to acquire uniform plasticity in order to be stretched over the model M. The heated and softened cone is manipulated with heat insulating gloves, by sliding it over the model M of slightly larger cross sectional configuration, whereby the cone stretches and constricts precisely to the model contours. The conformity of the cone C to the contours of model M is coextensive, including all draft angles positive or negative.

The aforesaid slide-on step is conducted as deftly and quickly as is conveniently possible and the cone C manipulated to exhaust any and all air pockets, so that interface contact of the heated cone C with the model M is coextensive and so that heat transfer into the model is ensured; the model having started at or near room temperature so as to act as a heat sink. Thus, the cone C now takes on the features necessary to the prosthesis and hardens to its prepared cured plastic state or condition constricting tightly onto model M by shrinkage, and adhearing mechanically to the model M. However, some heat is retained for removal of the prosthesis P from the model M in a warm condition, talc being employed at the interface between the model M and prosthesis P in order to facilitate removal as circumstances require.

The formed or reformed prosthesis P is now a socket S to be taken from or stripped from the model M, and in accordance with this invention by means of compressed air applied through a port 20 in the end wall 16 which displaces the prosthesis from the model. An air nozzle 21 is applied to the port 20 applying pneumatic force for ejection. Following the air ejection of the prosthesis from the model, the prosthesis P or socket S is permitted to return completely to ambient room temperature, after which it is trimmed and shaped by cutting, and abrading the edges thereof with a dry rag buffer wheel. Localized sculpting and reformation can be affected with a air heat gun or blower, providing localized temperature spots at about 3000° F. For example, the arm or leg openings will be flared and well rounded, and any apertures cut therein will be smoothed out.

The prosthesis socket S as it is dislosed herein is made of non toxic—non aromatic plastic material, it is fire retardent, it accepts adhesives, it is weldable and reformable at any time with the process steps as they are hereinabove disclosed. As shown there is a coupling 25 to which a simulated hand (or foot) is applied, and all of which can be augmented with articulation mechanisms as may be required.

Having described only a typical preferred form and application of my inventiion, I do not wish to be limited or restricted to the specific details herein set forth, but wish to reserve to myself any modifications or variations that may appear to those skilled in the art as set forth within the scope of the following claims.

I claim:

1. A reformable blank member to be made into a prosthesis conforming to a model of a person's body part, and including;
   a body of plastic material molded to the nominal wall thickness of the prosthesis and to the general configuration of said model and cured at a high temperature for rigidity at ambient room temperature, and conditioned to be made plastic at a high temperature substantially below the first mentioned curing temperature for subsequent conformity to said model and reset thereon at ambient room temperature for rigidity as a complete reshapable monolithic prosthesis.

2. The reformable blank member to be made into a monolithic prosthesis as set forth in claim 1, wherein the body of plastic material is vinyl.

3. The reformable blank member to be made into a monolithic prosthesis as set forth in claim 1, wherein the body of plastic material is principally of vinyl resin, a plasticizer and a stabilizer.

4. The reformable blank member to be made into a monolithic prosthesis as set forth in claim 1, wherein the body of plastic material is substantially 69.5% vinyl resin, 20.4% plasticizer, and 9.4% stabilizer.

5. A reformable cone shaped blank member to be made into a prosthesis socket conforming to a stump model of a person's body part, and including;
   a body of plastic material molded into a cone having the nominal wall thickness of the prosthesis and to the general but smaller cross sectional configuration than that of said model and cured at a high temperature for rigidity at ambient room temperature, and conditioned to be made plastic at a high temperature substantially below the first mentioned curing temperature for subsequent stretching over and into conformity to the configuration of said stump model and reset thereon at ambient room temperature for rigidity as a complete reshapable monolithic prosthesis socket.

6. The reformable blank member to be made into a monolithic prosthesis socket as set forth in claim 5, wherein the body of plastic material is vinyl.

7. The reformable blank member to be made into a monolithic prosthesis socket as set forth in claim 5, wherein the body of plastic material is principally of vinyl resin, a plasticizer and a stabilizer.

8. The reformable blank member to be made into a monolithic prosthesis socket as set forth in claim 5, wherein the body of plastic material is substantially 69.5% vinyl resin, 20.4% plasticizer, and 9.4% stabilizer.

* * * * *